(12) United States Patent
Dillon et al.

(10) Patent No.: US 7,821,634 B2
(45) Date of Patent: Oct. 26, 2010

(54) LASER-TRIGGERED PLASMA APPARATUS FOR ATOMIC EMISSION SPECTROSCOPY

(75) Inventors: Robert Dillon, Chelmsford, MA (US); Lee Grodzins, Lexington, MA (US); Stephanie Melikian, Somerville, MA (US)

(73) Assignee: Thermo Niton Analyzers LLC, Billerica, MA (US)

( * ) Notice: Subject to any disclaimer, the term of this patent is extended or adjusted under 35 U.S.C. 154(b) by 375 days.

(21) Appl. No.: 12/106,233

(22) Filed: Apr. 18, 2008

(65) Prior Publication Data

US 2008/0259330 A1    Oct. 23, 2008

Related U.S. Application Data

(60) Provisional application No. 60/925,383, filed on Apr. 20, 2007.

(51) Int. Cl.
*G01J 3/30* (2006.01)
(52) U.S. Cl. ...................................... 356/318
(58) Field of Classification Search ............... 356/318, 356/72
See application file for complete search history.

(56) References Cited

U.S. PATENT DOCUMENTS

| | | | |
|---|---|---|---|
| 3,597,086 A * | 8/1971 | Mela et al. ............ | 356/318 |
| 6,008,897 A * | 12/1999 | Sabsabi et al. ........ | 356/318 |
| 6,407,811 B1 | 6/2002 | Snyder et al. | |
| 7,420,663 B2 * | 9/2008 | Wang et al. ........... | 356/72 |
| 2004/0183018 A1 | 9/2004 | Zhou et al. | |
| 2008/0151241 A1 * | 6/2008 | Lindfors et al. ....... | 356/318 |

FOREIGN PATENT DOCUMENTS

WO    WO 2008/115287 A2    9/2008

OTHER PUBLICATIONS

Rasberry et al. "*Laser Probe Excitation in Spectrochemical Analysis. I: Characteristics of the Source*", Applied Optics, pp. 81-86, vol. 6, No. 1, Jan. 1967.
Lagalante "*Atomic Emission Spectroscopy: A Tutorial Review*", Applied Spectroscopy Review, pp. 191-207, vol. 34, No. 3, 1999.
Carranza et al. "*Plasma volume considerations for analysis of gaseous and aerosol sample using laser-induced breakdown spectroscopy*", J. Anal. At. Spectrom, pp. 1534-1539, vol. 17, 2002.
Rasberry et al., "Laser Probe Excitation in Spectrochemical Analysis. I: Characteristics of the Source," Applied Optics, vol. 6 ( No. 1), pp. 81-86, (1967).

* cited by examiner

*Primary Examiner*—Kara E Geisel
(74) *Attorney, Agent, or Firm*—Sunstein Kann Murphy & Timbers; Charles B. Katz

(57) ABSTRACT

Multiple energy sources, such as a laser and electrical current, are employed, in close coordination, spatially and temporally, to clean a sample, vaporize its material and excite vapor atoms for the purpose of atomic emission spectroscopy. These methods permit better monitoring and control of the individual processes in real time, lead to higher consistency and higher quality optical emission spectra, and enhance the measurements of non-conducting solids, liquids and gases. Additionally, a portable instrument is provided with both laser source and spectrometer optically coupled to a handholdable unit.

21 Claims, 4 Drawing Sheets

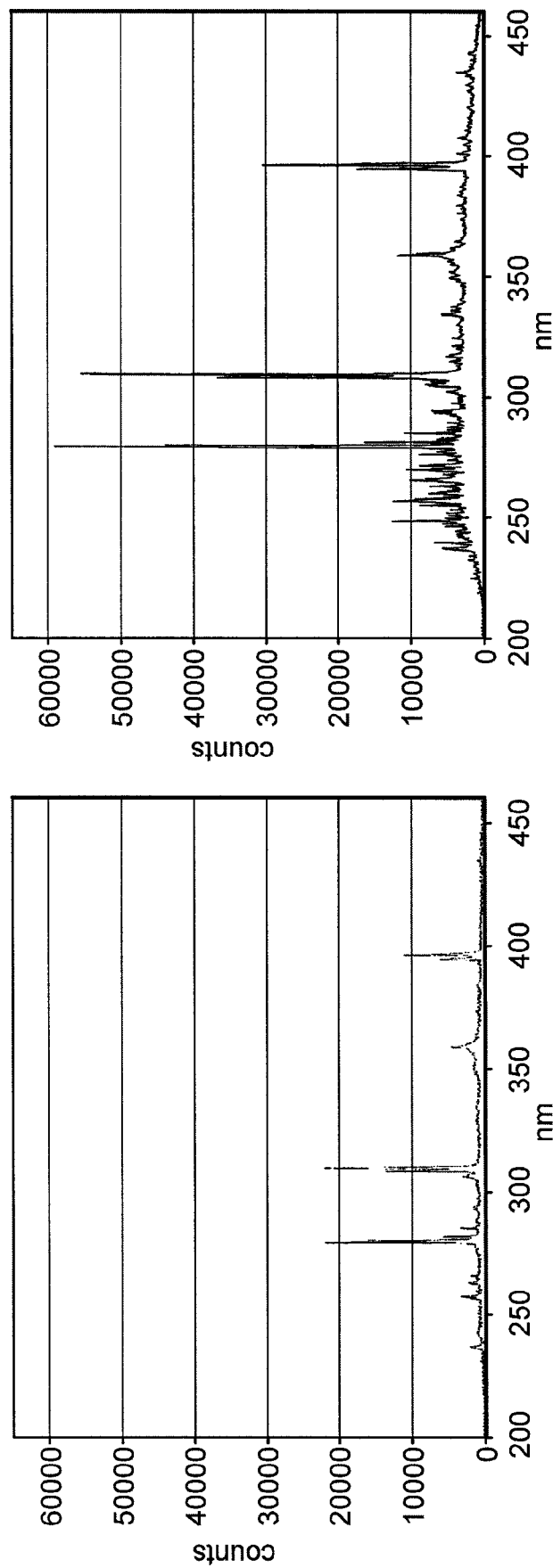

LASER-TRIGGERED PLASMA APPARATUS FOR ATOMIC EMISSION SPECTROSCOPY

The present application claims the priority of U.S. Provisional Patent Application Ser. No. 60/925,383, filed Apr. 20, 2007, which is incorporated herein by reference in its entirety.

TECHNICAL FIELD

The present invention relates to methods and devices for performing spectroscopic measurements of samples vaporized and excited through a combination of laser and spark excitation mechanisms, provided, in some embodiments, within a self-contained, hand-held instrument.

BACKGROUND ART

The field of atomic emission spectroscopy was developed at the time of Johann Balmer, Johannes Rydberg, Friedrich Paschen, and their contemporaries, during the late 1800s, when flame was used as an excitation source. Atomic emission spectroscopy is now applied to almost every scientific discipline including physics, astronomy, chemistry, biochemistry, medicine, forestry and agriculture, geology and mining, forensic science, environmental protection, metallurgy and metal production, etc. Innovations in this area are, therefore, significant and valuable.

Several methods are presently used to measure the optical emission spectra of solid, liquid and gas samples. Precision methods use a thermal (flame), electrical (arc/spark) or optical (laser) energy source to 1) remove debris from the sample surface, 2) heat a portion of the sample sufficiently to dissociate atoms in a gaseous vapor, and 3) excite the electron structure of the vapor atoms to temperatures sufficient to generate optical emission. A spectrometer records the resulting optical emission signatures.

Quantitative analysis emerged about 1930 with the use of alternating current (AC) arcs, interrupted direct current (DC) and AC arcs, as well as high voltage sparks. Sparks delivered sufficient energy to ionize sample vapors and reveal a wider array of emission lines. Electrical discharge (ED) techniques are widely used in some of the most precise analytical instruments built today, but application of ED techniques is limited to samples that are conductive. Such sources can deliver large energy to samples at low cost, and the energy delivery can be controlled to achieve high quality spectra. On the other hand, the precise location of plasma formation by ED techniques is difficult to control, making it, in turn, difficult to achieve high stability of the sensed optical signals. Indeed, erratic motion of the plasma location across the sample surface during the course of a measurement adds noise to the sensed optical signal. Moreover, the geometrical requirements, both with regard to sample proximity to the electrode and axial centering, limit the solid angle from which spectral signal may be obtained.

Within a decade of their advent, lasers were used as excitation sources for optical emission spectroscopy (OES), creating the field of Laser Induced Breakdown Spectroscopy (LIBS). This technique allows for fine spatial sampling of materials, since laser beams may be tightly focused and precisely directed. Moreover, LIBS imposes fewer geometrical restrictions on the signal acceptance angle, and, additionally, makes possible the practical measurement of nonconducting samples, including liquids and gases. LIBS equipment is expensive and far more complex than electrical discharge systems. At this time, the most precise results are obtained when multiple laser pulses are used, timed in rapid succession, and when "pre-ablation" laser pulses are delivered in the air above the sample prior to spectral measurement. Multiple laser pulses, delivered in rapid succession may require the use of multiple lasers, dramatically increasing the cost and complexity of such systems.

Rasberry et al., *Laser Probe Excitation In Spectrochemical Analysis*, Appl. Opt., vol. 6, pp. 81-86 (1967), incorporated herein by reference, reported the use of a laser providing energetic pulses of greater than 100 mJ per pulse to ablate significant quantities (e.g. 1.0 µg) of analyte and then to subsequently initiate electrical discharge in the resulting material-rich laser-induced plasma. The choice of excitation source was driven by its demonstrated ability to operate as a stand-alone LIBS source. In fact, the researchers routinely compared the spectra of laser-only (i.e. LIBS) optical emission with the spectra generated by laser-initiated electrical discharge (i.e. using electrodes to further excite the emissions).

All laser-excited OES practiced to date, whether in conjunction with electrical discharge or laser self-sustained, employs laser pulses of sufficient energy per pulse to ablate a volume of material from the surface of the sample that is adequate for spectroscopic observation. The term "ablation energy threshold," as used herein, and in any appended claims, refers to the instrument-specific minimum energy, per unit area of the sample, that is required in order to ablate atoms from the surface of the sample in sufficient number (typically greater than 1 microgram) and at sufficient quantum excitation to provide a signal-to-noise of at least unity in an atomic emission line in a single pulse. The ablation energy threshold depends on the material composition of the sample, on the spectral composition of the exciting pulse, and also, it has been shown, upon the pulse power and duration (and not merely upon their product).

The requirement, in all practice of LIBS to date, that the energy per pulse exceed the ablation energy threshold, imposes a lower limit on the size of laser that is required. Typically, energies per pulse in excess of 20 mJ are employed, and often substantially greater energy per pulse. A specific example of a laser routinely used for LIBS is the Big Sky Laser Technologies' Ultra Nd:YAG 50 mJ laser. The optical head size is 50 mm×75 mm×200 mm, and its controller/cooler unit measures 380 mm×380 mm×190 mm and dissipates>200W. This laser is water-cooled, requires regular periodic maintenance and will perform a maximum of 20 measurements per second.

The size and weight of lasers that are required by LIBS as currently practiced preclude hand-held practice of LIBS spectroscopy.

SUMMARY OF THE INVENTION

In accordance with preferred embodiments of the invention, a method and apparatus are provided for analyzing composition of a sample with an optical spectroscopic instrument. A method of the invention provides the following steps:

a. creating a plasma at a specified location in the gas proximate to an area at the surface of the sample by application of a first electromagnetic field characterized by a first spectral range and a second electromagnetic field characterized by a second spectral range, wherein at least one of the first and second electromagnetic fields is applied in a pulse of energy per unit area less than the threshold ablation energy associated with the sample in relation to the instrument; and b. detecting resonant emission emitted by atoms of the sample vaporized into the plasma.

In accordance with further embodiments of the invention, the first electromagnetic field may be an optical pulse of energy less that the threshold ablation energy, and the second electromagnetic field may be a static field. The first electromagnetic field may create a discharge within the gas and the second electromagnetic field additionally sustains the discharge. The step of creating a plasma may, more specifically, include irradiating the specified location with a laser beam.

Other embodiments of the invention may additionally entail applying a high-voltage bias across a spatial region prior to irradiating the specified location with the laser beam, wherein the high-voltage bias may be of constant polarity or of alternating polarity.

The method for analyzing composition of a sample may have a step of sustaining the plasma, which may include inducing a current between a pair of electrodes in a vicinity of the specified location. Creating the plasma may also include focusing a laser pulse with an optical element, while sustaining the plasma may include inducing a current between a plurality of pairs of electrodes jointly comprising an electrode structure in a vicinity of the specified location.

In other embodiments of the invention, the step of detecting resonant emission may include dispersing the emission in a spectrometer. A further step may provide for cleaning the surface with the discharge. Either a second laser pulse or a second arc discharge may be used to create a further discharge.

In accordance with another aspect of the invention, a method for analyzing composition of a sample with an optical spectroscopic instrument is provided that has steps of:
  a. applying an non-ionizing electrical bias field across a volume of the gas proximate to an area at the surface;
  b. triggering creation of a plasma at a specified location within the volume by application of an optical pulse; and
  c. detecting resonant emission emitted by atoms of the sample vaporized into the plasma.

The method may also include sustaining the plasma, and, more particularly, inducing a current between a plurality of pairs of electrodes jointly comprising an electrode structure in a vicinity of the specified location.

In accordance with yet another aspect of the present invention, a portable apparatus is provided for analyzing the composition of a sample. The apparatus has
  a. a hand-holdable unit for conducting spectrometric analysis in close proximity to the sample;
  b. a laser optically coupled to the hand-holdable unit for providing pulses of optical energy;
  c. an optical element disposed entirely within the hand-holdable unit for focusing the optical energy to create a plasma at a controlled location in a proximity of the sample;
  d. an electrode structure coupled to the hand-holdable unit for sustaining a discharge within the plasma;
  e. a spectrometer optically coupled to the hand-holdable unit for dispersing resonant emission emitted by atoms onto at least one detector; and
  f. a processor for receiving a signal from the at least one detector and determining, therefrom, a characteristic of the sample.

In other embodiments of the invention, the apparatus may also have a polarization control element for aligning polarization of the optical pulses in relation to the electrode structure, and a bias supply for applying an electric field across the controlled location in the proximity of the sample prior to providing successive pulses of optical energy.

BRIEF DESCRIPTION OF THE DRAWINGS

The foregoing features of the invention will be more readily understood by reference to the following detailed description, taken with reference to the accompanying drawings, in which:

FIG. 3(a) depicts laser induction of a plasma while FIG. 4(a) shows a spectrum of a sample of 6061 Aluminum alloy measured using prior art laser excitation techniques, while FIG. 4(b) shows a sample of the same alloy using discharge enhancement in accordance with an embodiment of the present invention.

DETAILED DESCRIPTION OF SPECIFIC EMBODIMENTS OF THE INVENTION

Preferred embodiments of the invention described herein are directed to the use of multiple energy sources to excite material for subsequent analysis of optical emission, obtaining advantages of synergy and eliminating some of the source-specific drawbacks. In accordance with certain of the preferred embodiments of the present invention, multiple energy sources are employed within a single hand-held or portable optical emission spectroscopy (OES) device in order to create a suitably energetic and controlled plasma for spectroscopic characterization.

Definitions: As used herein and in any appended claims, energy sources are distinct when their energy spectra are non-identical, whether or not their respective applications overlap in time. Moreover, the energy spectrum of one of the energy sources may include a static field, which may be characterized as a "DC" field, whether or not current is actually flowing, and without regard to the duration of time during which the static field is applied.

In particular, as fully discussed below, a laser serving as one energy source need not be particularly well suited or configured for accurate LIBS analysis to work well in an optimized apparatus in which an electrical discharge is laser-initiated. In fact, the optimal laser may not, in and of itself, generate useful emission spectra or ablate sufficient material to support high sensitivity LIBS-based analysis. Rather, the laser may operate with sufficient peak power density to form a conducting plasma (also referred to as 'breakdown') in close proximity to the analyte, but lack the time-integrated energy to ablate and excite material. Once a conducting path is formed, electrodes deliver high current to ablate material, heat the analyte-laden plasma and form high-quality emission spectra.

Figure 1:
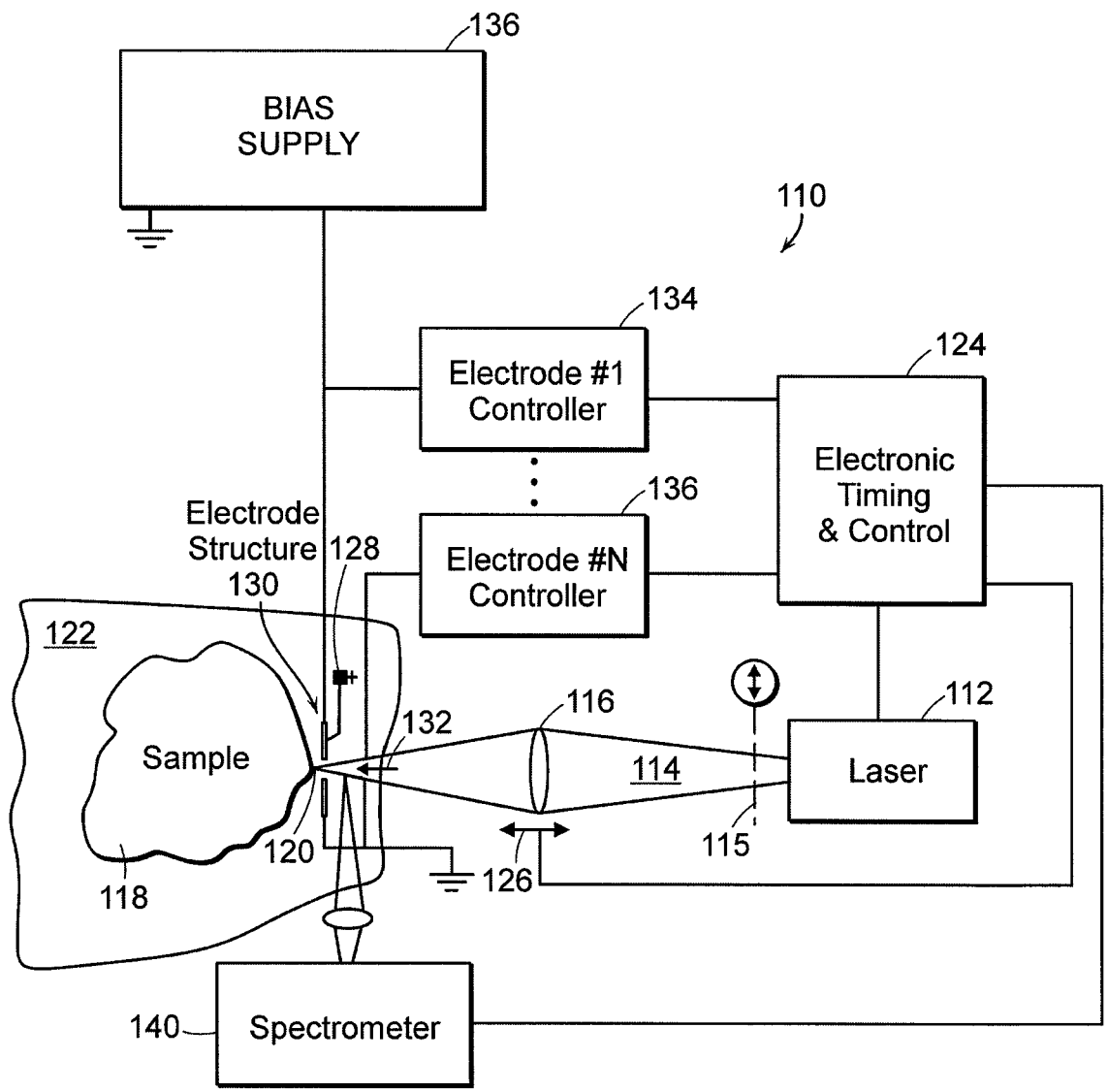
FIG. 1 is schematic depiction of a laser/spark sample excitation apparatus for practice of optical emission spectroscopy in accordance with embodiments of the present invention.

A general layout of a laser/spark OES system, designated generally by numeral 110, and as configured in accordance with embodiments of the present invention, is described with reference to FIG. 1. A laser 112 provides a beam 114 that is directed by optical element 116 to a controlled location 120 in the vicinity of the surface of sample 118. Laser 112 is preferably a pulsed laser, such as a periodically Q-switched laser, capable of pulsed, typically periodic, radiation in a specified portion of the electromagnetic (EM) spectrum, typically ultraviolet or visible, although operation in other part of the EM spectrum are also within the scope of the present invention.

Figure 2:
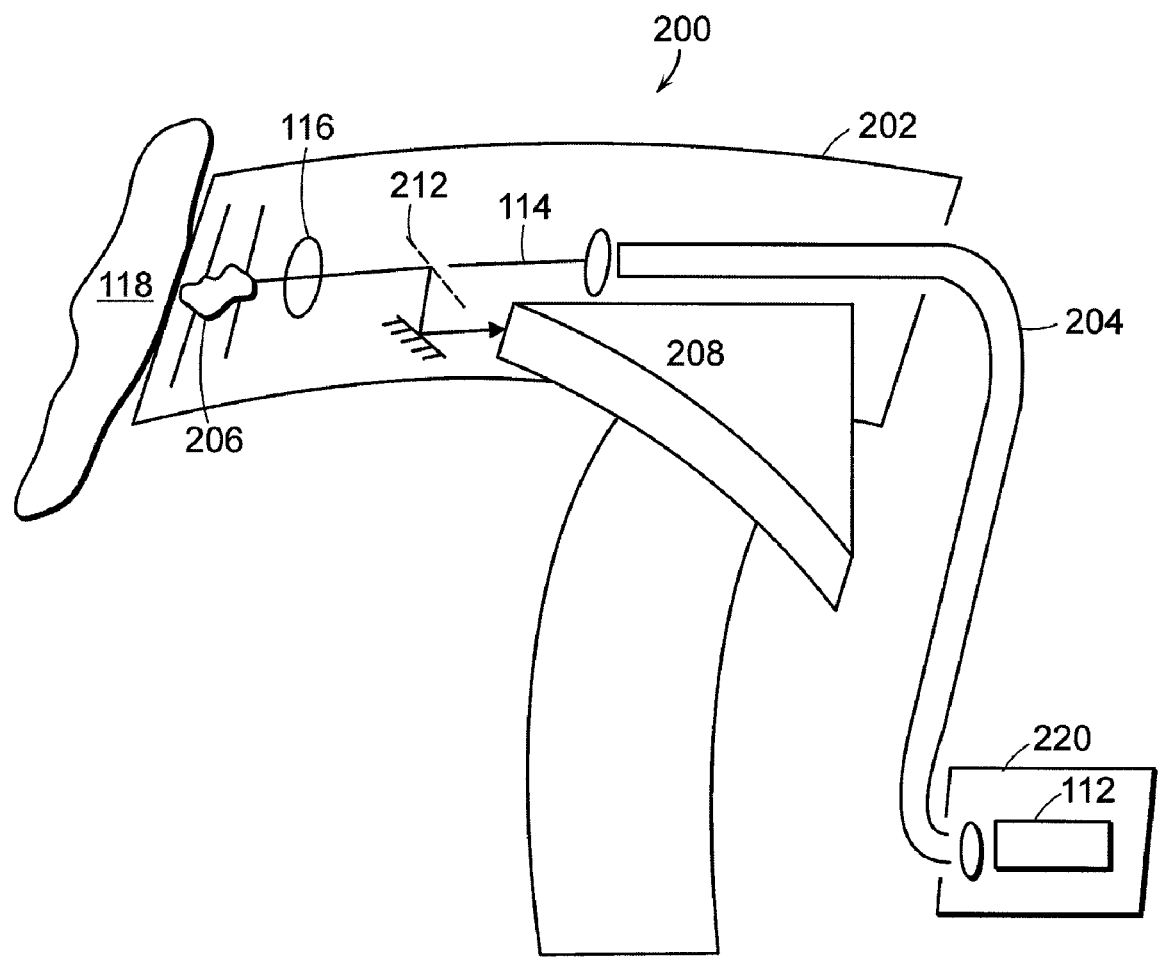
FIG. 2 is a schematic depiction of a hand-held laser/spark sample excitation apparatus in accordance with embodiments of the present invention.

Laser 112 may be contained entirely within a handheld unit, designated generally by numeral 200 and depicted schematically in FIG. 2.

Controlled focal location 120 is disposed within a gas 122 that is contained within, or flowed through, a region adjoining the surface of sample 118. During a portion of the pulse of laser 112, beam 114, focused at controlled location 120, induces breakdown of gas 122, at, or in the vicinity of, location 120. "Breakdown," as used herein, or in any appended claims, refers to a localized flow of current carried by charges induced in gas 122 through ionization due to an electric field, either the optical frequency electric field of beam 114, and/or another electric field. The field strength of the beam at location 120 at which breakdown of gas 122 occurs depends upon the composition and local pressure of gas 122, as well as upon the optical frequency (or frequencies, if laser 112 is polychromatic) of beam 114. A gas in which electrical charges have been separated and are not entirely bound to individual atoms may be referred to, herein and in any appended claims, as a "plasma." It is to be understood that the precise geometry of beam 114 at location 120 is governed by optical element 116, shown here, for purposes of exemplary representation only, as a lens. Optical element 116 may be any combination of reflective and/or transmissive optics, while the focal length, and, indeed, the number of foci, is within the scope of design choice by a person of ordinary skill in the optical arts. In certain embodiments of the invention, a lens of high numerical aperture (N.A.) is employed to achieve a tight focus, and a high power density within a small volume. The position and/or geometry the focus at controlled location 120 may be governed by a processor 124 adapted to govern the position of a focusing element (depicted, schematically, by double arrow 126).

Lasers of many types (actively Q-switched Nd:YAG & Nd:YLF lasers, passively Q-switched microchip lasers, for example) are powerful enough when coupled to high numerical aperture, low distortion optics to generate robust breakdown and plasma generation in a gas.

It is to be understood that the plasma need not be formed solely through interaction of the laser field with the gas. An electric field, either unipolar (DC) or alternating in polarity (AC) may be applied across location 120 by application of an electric potential to one or more electrodes 128, either relative to sample 118 (if it is conducting), or relative to one or more further electrodes. It is to be appreciated that, within the scope of the present invention, sample 118 may be a solid, liquid or gas, or suspension of one phase in another, such as an aerosol, a suspension of microspheres, etc. Under these circumstances, it is known that the optical field of beam 114 may initiate a breakdown of the gas, even at substantially lower beam power than would otherwise be required. Indeed, optically-triggered discharges have long been employed in such contexts as high-voltage switches, etc. This operation, in the context of the present invention, may be referred to as Laser Induced Discharge Spectroscopy (LIDS).

The one or more electrodes 128 are disposed in proximity to, and the general vicinity of, the surface of sample 118. Electrodes 128 may be configured, for example, in stacked electrode pairs, as shown, though various configurations of electrodes may form an electrode structure, designated generally by numeral 130. In exemplary embodiments of the invention, laser beam 114 is delivered through a passage 132 through electrode structure 130.

In other embodiments of the invention, a bias supply 136 coupled to electrodes 128 may provide an electric field, of constant or alternating polarity (i.e., either DC or AC), across a spatial region near the surface of the sample. The bias voltage is preferably set near, but below, the breakdown threshold of the surrounding gas, such that no plasma is formed in the absence of a laser pulse, however the energy requirements on the laser may thereby be advantageously reduced.

In accordance with certain embodiments of the invention, successive pairs of electrodes are each coupled electrically to an electrode controller 134, 136, capable of delivering current to its electrode pair. The controller 134, 136, in additional embodiments of the invention, may also be able to detect the electrical impedance in the gap between its two electrodes and/or control the current delivered to the electrode set as a function of time, based on timed commands from the electronic timing and control device 124. A spectrometer 140 is included to measure atomic emission spectra generated in the vicinity of the sample, receiving radiation from an appropriately chosen position along the electrode structure 130.

In various embodiments of the present invention, the polarization of laser beam 114 may be oriented, by means of a polarization control element 115, which may include a linearly polarized. ½-wavelength quartz wave plate, for example, placed in beam 114 after the laser 112, providing for control of the orientation of the beam's polarization, relative to the electrode structure, and thus the electric field, that provides bias or a sustaining field. The polarization may be adjusted at the time the unit is manufactured or calibrated or may be field-adjustable.

Returning to the portable OES analyzer 200 of FIG. 2, this embodiment of the present invention contains optical element 116 and spectrometer 208 within a single housing 202. Laser 112 may be contained either within housing 202 or within a readily portable external module 220, and optically coupled to analyzer 200 via an optical fiber 204. Beam 114 is coupled to optical element 116 via beamsplitter 212, which may be a half-silvered mirror, for example, and which also couples emission from plasma region 206 into spectrometer 208, preferably by a reflection path so as to avoid absorption of deeper UV photons due to transmission through a substrate.

Creation of a plasma by laser-induced breakdown, and subsequent sustenance and re-energizing of the plasma by current (direct or alternating) induced in the plasma by virtue of a voltage potential applied to one or more electrodes is now described with reference to FIGS. 3(a) and 3(b).

In accordance with embodiments of the present invention, plasmas generated initially by laser-induced breakdown may be further energized using a set of electrically charged electrodes 128 placed in proximity to the laser-induced plasma volume. Initial laboratory tests were successfully conducted using air, argon, paper, plastic and metal samples. The tests showed that plasmas generated by laser pulse energies may exhibit lower atomic excitation than those required for suitable LIBS measurements and may be electrically 're-energized' via electrodes to produce high intensity, high quality spectra.

Figure 3B:
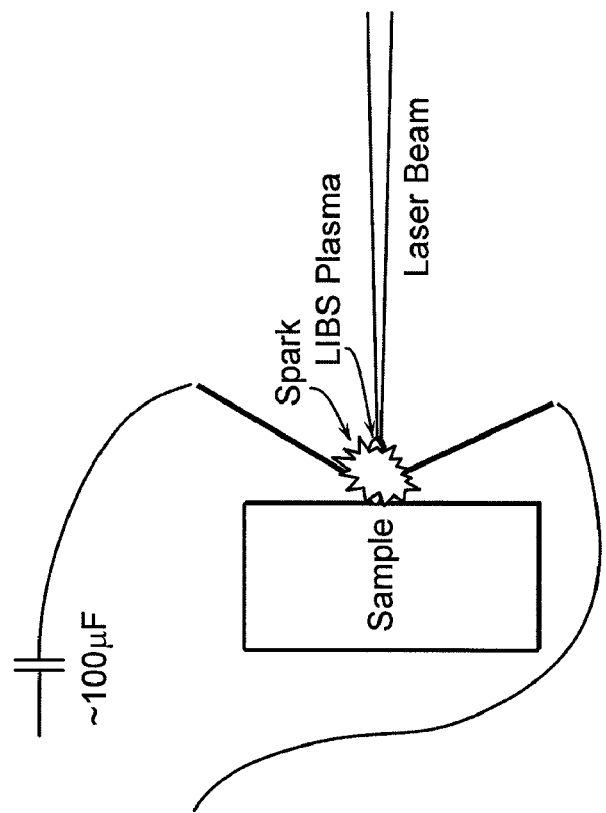
FIG. 3(b) depicts re-energizing the plasma my means of a discharge, both, in accordance with embodiments of the present invention.
Figure 3A:
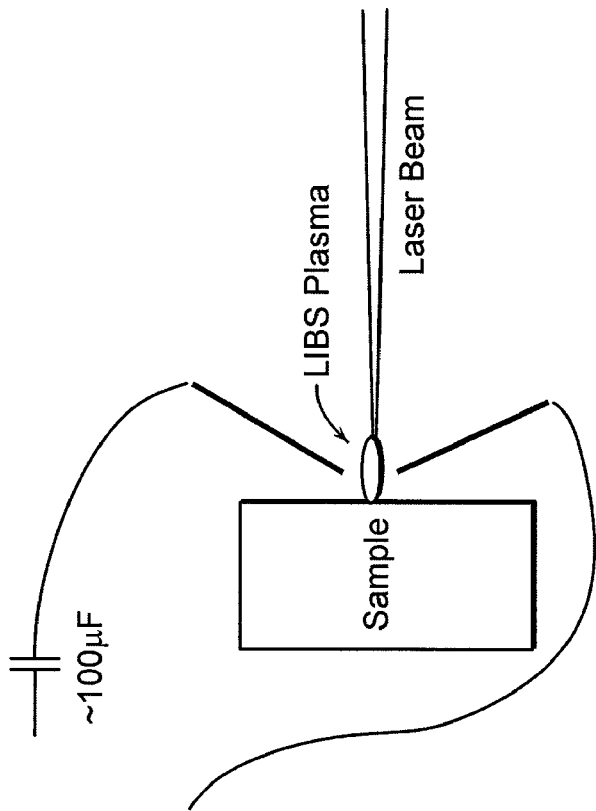

One embodiment of the method is illustrated schematically in FIGS. 3(a)-(b), where FIG. 3(a) shows a laser-induced discharge, while FIG. 3(b) depicts the subsequent re-energizing of the resultant plasma by charge delivered from a 100 μF capacitor. Examples of 6061 Aluminum spectra collected by the inventors are shown in FIGS. 4(a)-(b), measured without, and with, discharge enhancement, respectively. The tests revealed that relatively low electrode voltages produced significant spectral enhancement. Initial test conditions included a laser energy per pulse of ~15 mJ, a laser repetition rate of 2 Hz, a capacitance of 94 μF, across which a voltage of 70 V was applied. Air breakdown can also be initiated with pulses of energy less than 3 mJ.

In contradistinction to electrical initiation of a spark discharge in gas 120, laser initiation, in accordance with the present invention, can be directed to a precise location, and also scanned to multiple spatial locations under precise control. Also, the exact time of laser initiation can be controlled to great accuracies (nanoseconds) relative to its electrical counterpart (microseconds) permitting a high degree of control on the time at which one 're-energizes' the laser plasma with additional high-current electrical energy.

In accordance with alternate embodiments of the invention, airborne laser plasma is super heated by additional electrical energy (delivered through electrodes), and the resulting hot plasma is used to pre-ablate and clean the surface of a sample. Once the cleaning operation is completed, the laser plasma may be shifted closer to the sample by moving the focus lens shown in FIG. 1 where significantly greater amounts of sample volume are heated and analyzed by spectroscopic means. Alternatively, a discharge may be initiated between a set of electrodes disposed in closer proximity to the sample surface.

In accordance with embodiments of the present invention, laser 112 need only provide enough pulse power density to form the conducting plasma that can be further energized by electrical means, and that power density may be significantly reduced if an AC or DC field is already applied across the location 120 where the discharge is initiated. Our measurements show this occurs at a level of $\sim 5 \times 10^{12}$ W/cm$^2$ in air for laser wavelengths of 1064 nm, and at lower levels when other gases and solid materials are placed near the focal volume. Use of lower energy pulses greatly relieves constraints on the laser's size, weight, power consumption and waste heat generation, opening the door for portable and/or battery powered laser-initiated electrical discharge spectroscopy systems. For example, a small, passively Q-switched Nd:YAG laser operating at 100 μJ per pulse, 500 picoseconds pulse width, is able to generate the pulse power densities needed. With electrical discharge enhancement, the quality of spectra (signal strength, line width) exceeds that achievable with LIBS-sized lasers requiring ~10×the volume, weight and input power.

One example of a laser that could be used in an optimized laser-initiated electrical discharge system, based on the understandings of this invention, is the passively Q-switched microchip laser (such as may be obtained from TEEM Photonics), with a head size of ~25 mm×30 mm×175 mm, using a controller PCB sized at ~95 mm×95 mm×25 mm, dissipating<20 W. This laser requires only a small heat sink for sufficient cooling. It will perform 500 measurements per second.

It will be appreciated that the laser/spark technique and apparatus, described herein, in combining the laser-induced technique with the electrical discharge technique may advantageously derive benefits of each and overcome some of the disadvantages of each. In particular, the laser/spark retains the ability of LIBS to examine non-conducting solids, liquids and gases, while retaining the arc/spark's simplicity, ruggedness and low cost.

Moreover, laser 112 may be used to perform pre-ablation plus vapor/plasma generation; that is, the cleaning of the surface and the initial vaporization. The arc/spark then produces atomic excitation in a manner that may be advantageously controlled. The laser and arc/spark operations are independent and can be optimized for their specific purposes.

The combination of laser-triggered gas breakdown with DC or AC sustenance of the plasma significantly reduces the power requirements for the laser initiator compared to a pure LIBS system. The reduction in power, weight and size are critical to the commercial viability of hand-held or portable instruments, which is the preferred embodiment for laser/spark technique.

The electromagnetic radiation produced in a measurement is lower, by an order of magnitude or more, than that observed with a traditional spark-based OES. The reduction in weight, size and complexity of the EMI shielding required for spark-based OES is especially valuable for hand-held or portable instruments.

The laser/spark has pin-point spatial selectivity produced by the controlled pointing of the laser beam; the arc/spark technique does not. This feature is expected to be especially useful for hand-held instruments used in the field, where the material being examined is a part of a complex of materials.

Laser/spark retains the important advantage of LIBS to ablate a much smaller amount of material for a given measurement than is possible with traditional arc/spark, which typically "destroys" an area of at least 25 mm$^2$. The precisely-directed laser pulse defines the point of ablation and therefore the point of arc excitation. Multiple laser/arcs can be carried out on the same initial point making the method close to "non-destructive", which significantly increases the applications of laser/spark, especially for field use, an important commercial advantage. The laser/spark retains the advantage of LIBS to spatially profile or spatially average the sampling by scanning the laser beam.

A single laser can be used with several or many spark gaps to monitor and control the temporal and spatial characteristics of ionized vapors emerging from a sample.

The optical spectrum from the laser contains information that is useful in complementing analysis of the later, and independent, optical spectrum from the spark The described embodiments of the invention are intended to be merely exemplary and numerous variations and modifications will be apparent to those skilled in the art. All such variations and modifications are intended to be within the scope of the present invention as defined in the appended claims.

We claim:

1. A method for analyzing composition of a sample with an optical spectroscopic instrument, the sample characterized by a threshold ablation energy per unit area with respect to the instrument, and by a surface at an interface between the sample and a gas, the method comprising:
    a. creating a plasma at a specified location in the gas proximate to an area at the surface of the sample by application of a first electromagnetic field characterized by a first spectral range and a second electromagnetic field characterized by a second spectral range, wherein at least one of the first and second electromagnetic fields is applied in a pulse of energy per unit area less than the threshold ablation energy; and
    b. detecting resonant emission emitted by atoms of the sample vaporized into the plasma.

2. A method in accordance with claim 1, wherein the first electromagnetic field is an optical pulse of energy less that the threshold ablation energy.

3. A method in accordance with claim 1, wherein the second electromagnetic field is a static field.

4. A method in accordance with claim 1, wherein the first electromagnetic field creates a discharge within the gas and the second electromagnetic field additionally sustains the discharge.

5. A method in accordance with claim 1, wherein the step of creating a plasma includes irradiating the specified location with a laser beam.

6. A method in accordance with claim 5, further comprising applying a high-voltage bias across a spatial region prior to irradiating the specified location with the laser beam.

7. A method in accordance with claim 6, wherein the high-voltage bias is of constant polarity.

8. A method in accordance with claim 6, wherein the high-voltage bias is of alternating polarity.

9. A method in accordance with claim 1, further comprising a step of sustaining the plasma.

10. A method in accordance with claim 9 wherein the step of sustaining the plasma includes inducing a current between a pair of electrodes in a vicinity of the specified location.

11. A method in accordance with claim 1, wherein the step of creating a plasma includes focusing a laser pulse with an optical element.

12. A method in accordance with claim 9, wherein the step of sustaining the plasma includes inducing a current between a plurality of pairs of electrodes jointly comprising an electrode structure in a vicinity of the specified location.

13. A method in accordance with claim 1, wherein the step of detecting resonant emission includes dispersing the emission in a spectrometer.

14. A method in accordance with claim 1, further including a step of cleaning the surface with the discharge.

15. A method in accordance with claim 8, further including a step of creating a further discharge by means of either a second laser pulse or a second arc discharge.

16. A method for analyzing composition of a sample with an optical spectroscopic instrument, the sample characterized by a surface at an interface between the sample and a gas, the method comprising:
   a. applying an non-ionizing electrical bias field across a volume of the gas proximate to an area at the surface;
   b. triggering creation of a plasma at a specified location within the volume by application of an optical pulse; and
   c. detecting resonant emission emitted by atoms of the sample vaporized into the plasma.

17. A method in accordance with claim 16, further comprising a step of sustaining the plasma.

18. A method in accordance with claim 17, wherein the step of sustaining the plasma includes inducing a current between a plurality of pairs of electrodes jointly comprising an electrode structure in a vicinity of the specified location.

19. A portable apparatus for analyzing composition of a sample characterized by a threshold ablation energy and by a surface at an interface between the sample and a gas, the apparatus comprising:
   a. a hand-holdable unit for conducting spectrometric analysis in close proximity to the sample;
   b. a laser optically coupled to the hand-holdable unit for providing pulses of optical energy;
   c. an optical element disposed entirely within the hand-holdable unit for focusing the optical energy to create a plasma at a controlled location in a proximity of the sample;
   d. an electrode structure coupled to the hand-holdable unit for sustaining a discharge within the plasma;
   e. a spectrometer optically coupled to the hand-holdable unit for dispersing resonant emission emitted by atoms onto at least one detector; and
   f. a processor for receiving a signal from the at least one detector and determining, therefrom, a characteristic of the sample.

20. An apparatus in accordance with claim 19, further comprising a polarization control element for aligning polarization of the optical pulses in relation to the electrode structure.

21. An apparatus in accordance with claim 19, further comprising a bias supply for applying an electric field across the controlled location in the proximity of the sample prior to providing successive pulses of optical energy.

* * * * *